United States Patent [19]

Van Eyck et al.

[11] 4,062,833
[45] Dec. 13, 1977

[54] BIURET POLYISOCYANATES

[75] Inventors: Michael J. Van Eyck; Kenneth A. Burdett, both of Midland, Mich.

[73] Assignee: The Dow Chemical Company, Midland, Mich.

[21] Appl. No.: 716,850

[22] Filed: Aug. 23, 1976

[51] Int. Cl.$^2$ .......................................... C07C 119/042
[52] U.S. Cl. ...................... 260/77.5 AT; 260/453 AB
[58] Field of Search ................. 260/453 AB, 77.5 AT

[56] References Cited

U.S. PATENT DOCUMENTS 3,903,127   9/1975   Wagner et al. ............... 260/453 AB Primary Examiner—Dolph H. Torrence
Attorney, Agent, or Firm—L. Wayne White

[57] ABSTRACT

The biuret polyisocyanates correspond to the formula

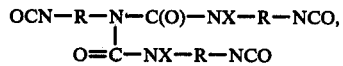

wherein R is —CH$_2$CH$_2$—O—CH$_2$CH$_2$— and X is hydrogen or —C(O)—NX—R—NCO, and they have not more than six isocyanato groups per molecule. These compounds are prepared by reacting bis(2-isocyanatoethyl)ether with water in a mole ratio of at least 3 moles of diisocyanate per mole of water. The biuret polyisocyanates are particularly useful in the preparation of polyurethanes.

4 Claims, No Drawings

BIURET POLYISOCYANATES

BACKGROUND OF THE INVENTION

1. Field of the Invention

This invention pertains to novel biuret polyisocyanates which are useful in preparing non-yellowing polyurethanes.

2. Description of the Prior Art

A variety of biuret polyisocyanates have previously been prepared by reacting an organic diisocyanate with water (U.S. Pat. Nos. 3,124,605 and 3,903,127), formic acid (U.S. Pat. No. 3,350,438), tertiary alcohols (U.S. Pat. No. 3,358,010) monoamines (U.S. Pat. No. 3,392,183), diamines (U.S. Pat. Nos. 3,441,588 and 3,903,126), ureas (U.S. Pat. No. 3,367,956 and U.K. Pat. Specification No. 1,043,674), and other biuretizing agents (U.S. Pat. No. 3,903,127).

Biuret polyisocyanates react with compounds bearing active hydrogen to form polyurethanes, polyureas, etc., as illustrated by U.S. Pat. No. 3,201,372, the disclosure of which is incorporated herein by reference. The biuret polyisocyanate derived from hexamethylene diisocyanate is taught to be the preferred biuret polyisocyanate for use in making polyurethanes in U.S. Pat. No. 3,201,372.

The major problems associated with the prior art compositions and processes are: (1) extremely high viscosities, and (2) the formation of insoluble ureas when water was used as the biuretizing agent. Such insoluble materials must be filtered from the final product.

SUMMARY OF THE INVENTION

A novel class of biuret polyisocyanates has now been discovered whose members have not more than six isocyanato groups and correspond to the formula:

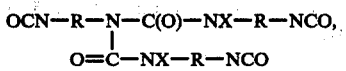

wherein R is —CH$_2$CH$_2$—O—CH$_2$CH$_2$— and X is hydrogen or —C(O)—NX—R—NCO. These biuret isocyanates are readily prepared by reacting bis(2-isocyanatoethyl)ether with water in a mole ratio of at least about 3 moles of diisocyanate per mole of water. The reaction is a very facile reaction and, surprisingly, does not produce any insoluble ureas. The new biuret polyisocyanates are extremely useful in reaction with polyols to form new polyurethanes. The reactivity of the isocyanato groups on both the bis(2-isocyanatoethyl)ether reactant and the isocyanato groups on the biuret polyisocyanates with hydroxyl groups is surprisingly high.

The novel class of biuret polyisocyanates also have better color and lower product viscosities at equal isocyanate/water ratios, better thermal stability, better shelf life stability, better compatibility with organic solvents, better compatibility with compounds containing active hydrogen (such as the polyhydric polyethers, polyhydric phenols, polyhydric polyesters, etc.), and better product purity. Further, the present class of biuret polyisocyanates are obtained in better product yield, based on water, than the corresponding biuret polyisocyanates prepared from hexamethylene diisocyanate and water. All of these advantages are commercially significant.

DETAILED DESCRIPTION OF THE INVENTION

The biuret polyisocyanates here described are readily prepared by reacting bis(2-isocyanatoethyl)ether with water. This reaction is conducted by merely blending the reactants at a mole ratio of at least 3 moles of the diisocyanate per mole of water and heating the reaction mixture at a temperature from about 80° to about 105° C. Normally, this reaction is conducted under an inert atmosphere (e.g., nitrogen) to reduce the formation of oxidized by-products. If excess diisocyanate is used in the reaction, the excess is removed from the desired biuret polyisocyanate by heating the reaction mixture under reduced pressure. The diisocyanate is thus removed as a volatile gas and leaves the biuret polyisocyanate a viscous liquid. The viscous liquid consists primarily of the trimeric biuret polyisocyanate (corresponding to the above formula wherein X is hydrogen).

The bis(2-isocyanatoethyl)ether is a known compound and can be prepared by reacting phosgene with bis(2-aminoethyl)ether or the hydrochloride salt thereof in a conventional solvent (e.g., chlorobenzene) at elevated temperatures.

The biuret polyisocyanates are used in the preparation of new urethanes by reacting the biuret polyisocyanates with polyhydric containing materials under conventional conditions; as set forth, for example, in U.S. Pat. No. 3,201,372.

EXPERIMENTAL

The following examples will further illustrate the invention.

EXAMPLE 1

Bis(2-isocyanatoethyl)ether (78 g, 0.5 moles) was charged to a reaction vessel equipped with a magnetic stirrer, nitrogen bubbler, thermometer, condenser and water inlet. The material was heated to 80° C under a stream of nitrogen and water (1.8 g, 0.1 mole) was added dropwise in a period of approximately 30 minutes. Heating at 80° C was continued for 1 hour followed by 2 hours at 105° C. The reaction vessel was then fitted with a distillation head and excess bis(2-isocyanatoethyl)ether removed from the clear, colorless solution by distillation at 105° C/0.1 mm Hg. The biuret polyisocyanate was thus obtained as a clear colorless liquid (30 g) having a viscosity of 10,361 cps at 22° C and an isocyanate content of 21.3 weight percent. This amounts to a 68 percent yield, based on water added.

EXAMPLE 2

The procedure in Example 1 was followed except the molar ratio of diisocyanate to water was adjusted to 10 moles of diisocyanate per mole of water. The clear, pale yellow residue thus obtained was further purified by use of a falling film still at 136° C/0.1 mm. The material thus obtained weighed 356 g and had a viscosity of 1,000 cps at 22° C and an isocyanate content of 24.4 weight percent (80 percent yield, based on water).

EXAMPLE 3

Following the procedures of Example 2 except the molar ratio was adjusted to 15 moles of diisocyanate per mole of water, the product was obtained as a clear yellow liquid with a viscosity of 700 cps at 22° C. The isocyanate content and yield were essentially the same as Example 2.

EXAMPLE 4

Following substantially the same procedure set forth in Example 2, the diisocyanate was reacted with water in a mole ratio of 20:1 for 2.2 hours at 80° C and then at 105° C for 3 hours. The crude reaction product was purified according to the procedure in Example 2. The product was thus obtained as a pale yellow liquid weighing 105 g and having a viscosity of 672 cps at 22° C and an isocyanate content of 25 weight percent (82 percent yield, based on water).

COMPARATIVE EXAMPLE

Hexamethylene diisocyanate was reacted with water under essentially the same conditions as set forth in Examples 1 and 2 above using various ratios of reactants. Table 1 below shows the differences in viscosities of the biuret polyisocyanates prepared from bis(2-isocyanatoethyl)ether and hexamethylene diisocyanate.

Table I

| Molar Ratio | Viscosity (cps) at 22° C | |
|---|---|---|
| | HMDI/H$_2$O | BIEE/H$_2$O |
| 5:1 | 12,500 | 10,000 |
| 10:1 | 6,200 | 1,000 |
| 15:1 | 1,480 | 700 |
| 20:1 | | 672 |

In Table 1, the values under the heading "molar ratio" refer to the molar ratio of diisocyanate to water in the preparation of the biuret polyisocyanate. HMDI and BIEE stand for hexamethylene diisocyanate and bis(2-isocyanatoethyl)ether, respectively.

The data in Table 1 clearly show that the biuret polyisocyanates prepared from bis(2-isocyanatoethyl)ether and water are substantially less viscous than the materials prepared from hexamethylene diisocyanate and water at the same molar ratios. This is very important from a procedural standpoint since the less viscous materials are easier to blend, etc. For example, we observed that the biuret polyisocyanate prepared from the bis(2-isocyanatoethyl)ether dissolved three to four times faster in various polyols than a commercial biuret polyisocyanate prepared from hexamethylene diisocyanate and water. We also observed that materials formed bis(2-isocyanatoethyl)ether and water contained no insoluble ureas and required no filtration. The biuret polyisocyanates prepared from hexamethylene diisocyanate, on the other hand, required filtration in all instances to remove insoluble ureas formed during reaction. We further observed that our materials were stable for 25 weeks at 50° C; i.e., they lost only about 4 percent isocyanate and did not change color. The commercial product prepared from hexamethylene diisocyanate, on the other hand, solidified within a 7-week period. A commercial sample referred to above was from Mobay and is referred to as Desmodur N-100 ®.

We claim:

1. A compound having not more than six isocyanato groups and corresponding to the formula:

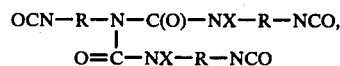

wherein:

R is —CH$_2$CH$_2$—O—CH$_2$CH$_2$— and X is hydrogen or —C(O)—NX—R—NCO.

2. The compound defined by claim 1 wherein X is hydrogen.

3. The product produced by reacting by contacting (a) OCN—CH$_2$CH$_2$—O—CH$_2$CH$_2$—NCO with (b) water in a molar ratio of at least about 3 moles of (a) per mole of (b).

4. In a process for making a biuret polyisocyanate-based polyurethane which comprises reacting an organic biuret polyisocyanate with an organic compound having at least 2 reactive hydrogen atoms, as determined by the Zerewitinoff procedure, the improvement comprising using the compound defined by claim 1 as the biuret polyisocyanate.

* * * * *